(12) United States Patent
Amako et al.

(10) Patent No.: US 9,151,666 B2
(45) Date of Patent: Oct. 6, 2015

(54) SENSOR CHIP, SENSOR CARTRIDGE, AND ANALYSIS APPARATUS

(71) Applicant: Seiko Epson Corporation, Tokyo (JP)

(72) Inventors: Jun Amako, Matsumoto (JP); Kohei Yamada, Minowa (JP)

(73) Assignee: Seiko Epson Corporation (JP)

(*) Notice: Subject to any disclaimer, the term of this patent is extended or adjusted under 35 U.S.C. 154(b) by 352 days.

(21) Appl. No.: 13/858,323

(22) Filed: Apr. 8, 2013

(65) Prior Publication Data
US 2013/0229652 A1 Sep. 5, 2013

Related U.S. Application Data

(63) Continuation of application No. 12/947,888, filed on Nov. 17, 2010, now Pat. No. 8,415,611.

(30) Foreign Application Priority Data

| Nov. 19, 2009 | (JP) | 2009-263706 |
| Dec. 11, 2009 | (JP) | 2009-281480 |
| Aug. 30, 2010 | (JP) | 2010-192838 |
| Aug. 30, 2010 | (JP) | 2010-192839 |

(51) Int. Cl.
*G01D 5/36* (2006.01)
*G01J 1/04* (2006.01)
(Continued)

(52) U.S. Cl.
CPC .............. *G01J 1/0407* (2013.01); *G01N 21/55* (2013.01); *G01N 21/553* (2013.01); *G01N 21/658* (2013.01); *G01N 21/774* (2013.01)

(58) Field of Classification Search
CPC .... G01N 21/658; G01N 21/774; G01N 21/55
USPC ............ 250/237 G, 237 R, 573, 576; 349/96; 359/486, 569
See application file for complete search history.

(56) References Cited

U.S. PATENT DOCUMENTS 4,674,878 A * 6/1987 Vo-Dinh ...................... 356/301
5,255,067 A * 10/1993 Carrabba et al. ............. 356/301
(Continued)

FOREIGN PATENT DOCUMENTS

| JP | 10-274631 | 10/1998 |
| JP | 2000-356587 | 12/2000 |

(Continued)

OTHER PUBLICATIONS

Andreas Heinz Nicol, "Grating Coupled Surface Plasmon Enhanced Flourescence Spectroscopy", Sep. 2005, (URL: http://www2.mpip-mainz.de/groups/knoll/publication/theses/2005/nicol_2005), pp. 1-11.

(Continued)

*Primary Examiner* — Seung C Sohn
(74) *Attorney, Agent, or Firm* — Harness, Dickey & Pierce, P.L.C.

(57) ABSTRACT

A sensor chip includes: a substrate that has a planar portion; and a diffraction grating on the planar portion and having a metal surface, the diffraction grating having a target substance thereon and including: a plurality of first protrusions periodically arranged in a period equal to or greater than 100 nm and equal to or less than 1000 nm in a first direction parallel to the planar portion, a plurality of base portions located between two adjacent first protrusions and configures abase of the substrate, a plurality of second protrusions formed on upper faces of the plurality of first protrusions, and a plurality of third protrusions formed on the plurality of base portions.

16 Claims, 13 Drawing Sheets

(51) Int. Cl.
  *G01N 21/552* (2014.01)
  *G01N 21/65* (2006.01)
  *G01N 21/77* (2006.01)
  *G01N 21/55* (2014.01)

(56) References Cited

U.S. PATENT DOCUMENTS

| | | | |
|---|---|---|---|
| 5,477,351 | A | 12/1995 | Takahara et al. |
| 5,986,762 | A | 11/1999 | Challener |
| 6,810,057 | B1 | 10/2004 | Itoh et al. |
| 6,861,263 | B2 * | 3/2005 | Natan ............... 436/164 |
| 7,388,661 | B2 | 6/2008 | Li et al. |
| 7,722,194 | B2 | 5/2010 | Amako et al. |
| 7,755,718 | B2 | 7/2010 | Amako et al. |
| 7,972,017 | B2 | 7/2011 | Amako et al. |
| 8,154,722 | B2 * | 4/2012 | Yamada et al. ........ 356/301 |
| 8,208,191 | B2 | 6/2012 | Gan et al. |
| 8,221,963 | B2 | 7/2012 | Amako et al. |
| 8,323,564 | B2 | 12/2012 | Padmanabhan et al. |
| 8,415,611 | B2 | 4/2013 | Amako et al. |
| 2004/0155309 | A1 | 8/2004 | Sorin et al. |
| 2008/0218761 | A1 | 9/2008 | Nishikawa et al. |
| 2008/0304004 | A1 | 12/2008 | Amako et al. |
| 2009/0170038 | A1 | 7/2009 | Amako et al. |
| 2010/0020400 | A1 | 1/2010 | Amako |
| 2010/0188747 | A1 | 7/2010 | Amako et al. |
| 2010/0238555 | A1 | 9/2010 | Amako et al. |
| 2011/0114859 | A1 | 5/2011 | Amako et al. |
| 2011/0116088 | A1 | 5/2011 | Amako et al. |
| 2012/0091372 | A1 | 4/2012 | Molnar et al. |

FOREIGN PATENT DOCUMENTS

| | | | |
|---|---|---|---|
| JP | 2001-242314 | A | 9/2001 |
| JP | 2006-091204 | A | 4/2006 |
| JP | 2008-203553 | | 9/2008 |
| JP | 2009-015302 | | 1/2009 |
| JP | 2009-015305 | | 1/2009 |
| JP | 2009-064005 | | 3/2009 |
| JP | 2009-134287 | | 6/2009 |
| JP | 2009-175707 | | 8/2009 |
| JP | 2009-222507 | A | 10/2009 |
| JP | 2009-250951 | A | 10/2009 |

OTHER PUBLICATIONS

Extended European Search Report for Application No. 10 19 1512 mailed Sep. 3, 2012 (9 pages).

Heinz, Andreas Nicol, "Grating Coupled Surface Plasmon Enhanced Fluorescence Spectroscopy", Johannes Gutenberg—Universität Mainz, Germany, Nov. 11, 2005, p. 1-169.

Kubo, Atsushi, et al. "Femtosecond Microscopy of Localized and Propagating Surface Plasmons in Silver Gratings", Journal of Physics B, Atomic, Molecular and Optical Physics, Institute of Physics Publishing, Bristol, GB, vol. 40, No. 11, Jun. 14, 2007, Sections 1 and 3.1 pp. S259-S272.

Extended European Search Report for Application No. 10 19 1511 mailed Sep. 3, 2012 (7 pages).

Barnes, William L. et al., "Surface Plasmon Subwavelength Optics", Nature: International Weekly Journal of Science, Nature Publishing Group, United Kingdom, vol. 424, Aug. 14, 2003, pp. 824-830.

Li, Lifeng, et al., "Convergence of the Coupled-Wave Method for Metallic Lamellar Diffraction Gratings", Optical Society of America, Optical Sciences, Center, University of Arizona, vol. 10, No. 6, Jun. 1993, pp. 1184-1189.

* cited by examiner

SENSOR CHIP, SENSOR CARTRIDGE, AND ANALYSIS APPARATUS

CROSS REFERENCES TO RELATED APPLICATIONS

This is a continuation application of U.S. Ser. No. 12/947,888 filed Nov. 17, 2010, which claims priority to Japanese Patent Application Nos. 2009-281480 filed Dec. 11, 2009, 2009-263706 filed Nov. 19, 2009, 2010-192838 filed Aug. 30, 2010, and 2010-192839 filed Aug. 30, 2010 all of which are incorporated herein by reference in their entireties.

BACKGROUND

1. Technical Field

The invention relates to a sensor chip, a sensor cartridge, and an analysis apparatus.

2. Related Art

Recently, demand for sensors used in medical diagnoses, the inspection of food, and the like has been increasing, and thus development of sensor technology that implements a sensor that is miniaturized and capable of sensing at high speed has been demanded. In order to respond to such demands, various types of sensors using electrochemical techniques and the like have been reviewed. Among these, from the viewpoint of easy integration, low cost, and low sensitivity to the measurement environment, sensors using surface plasmon resonance (SPR) have drawn attention.

Here, the surface plasmon is an oscillation mode of an electron wave that is coupled with light depending on boundary conditions specific to the surface. As a method of exciting the surface plasmon, there is a method in which a diffraction grating is imprinted on a metal surface and light and plasmon are coupled together or a method in which an evanescent wave is used. For example, as a configuration of a sensor that uses SPR, a configuration in which a total reflection-type prism and a metal film brought into contact with a target substance that is formed on the surface of the prism are included is known. According to such a configuration, whether or not a target substance is adsorbed is detected, including whether or not an antigen is adsorbed in an antigen-antibody reaction and the like.

However, while propagation-type surface plasmon exists on the metal surface, localized-type surface plasmon exists in a metal fine particle. It is known that, when the localized-type surface plasmon, that is, the surface plasmon that exists locally on the microstructure of the surface is excited, a markedly enhanced electric field is generated.

Thus, in order to improve the sensitivity of the sensor, a sensor that uses a localized surface plasmon resonance (LSPR) using metal fine particles or metal nanostructures is proposed. For example, in JP-A-2000-356587, by irradiating light onto a transparent substrate having a surface to which metal fine particles are fixed in a film shape and measuring the absorbance of light being transmitted through the metal fine particles, a change in the medium near the metal fine particles is detected, whereby adsorption or deposition of a target substance is detected.

However, according to JP-A-2000-356587, it is difficult to produce metal fine particles that have a uniform size (dimension or shape) and to regularly arrange the metal fine particles. When the size or the arrangement of the metal fine particles cannot be controlled, there are variations in absorption due to resonance or a resonant wavelength. Accordingly, the width of the absorbance spectrum becomes broad, and the peak intensity decreases. Accordingly, a change in the signal detecting the change in the medium near the metal fine particles is low, and there are limitations on improving the sensitivity of the sensor. Therefore, the sensitivity of the sensor is insufficient for use in specifying a substance from the absorbance spectrum or the like.

SUMMARY

An advantage of some aspects of the invention is that it provides a sensor chip, a sensor cartridge, and an analysis apparatus capable of specifying a target substance from a Raman spectroscopic spectrum by improving the sensitivity of a sensor.

Aspects of the invention employ the following configurations.

According to a first aspect of the invention, there is provided a sensor chip including: a substrate that has a planar portion; and a diffraction grating on the planar portion and having a metal surface, the diffraction having a target substance thereon and including: a plurality of first protrusions periodically arranged in a period equal to or greater than 100 nm and equal to or less than 1000 nm in a first direction that is parallel to the planar portion, a plurality of base portions located between two adjacent first protrusions and configures a base of the substrate, a plurality of second protrusions on upper faces of the plurality of the first protrusions, and a plurality of third protrusions on the plurality of base portions.

According to the first aspect of the invention, a proximal electric field that is enhanced through surface plasmon resonance by the first protrusions is excited toward the surface having the same shape, and surface enhanced Raman scattering (SERS) having a high degree of enhancement can be further exhibited by a metallic microstructure according to the second protrusions and the third protrusions. More specifically, when light is incident to a surface on which a plurality of the first protrusions, a plurality of the second protrusions, and a plurality of the third protrusions are formed, a surface-specific oscillation mode (surface plasmon) is formed by the plurality of the first protrusions. Then, free electrons are in a state of resonant oscillation accompanying the oscillation of light, and accordingly, the oscillation of an electromagnetic wave is excited accompanying the oscillation of the free electrons. Since the oscillation of the free electrons is influenced by the oscillation of this electromagnetic wave, a system acquired by coupling the oscillations of both parties, that is, a so-called surface plasmon polariton (SPP) is formed. Accordingly, localized surface plasmon resonance (LSPR) is excited near the plurality of the second protrusions and the plurality of the third protrusions. In this structure, since the distance between two of the second protrusions adjacent to each other and the distance between two of the third protrusions adjacent to each other are short, an extremely strong enhanced electric field is generated near the contact points thereof. Then, when one to several target substances are adsorbed on the contact points, the SERS occurs from the contact points. Accordingly, a sharp SERS spectrum that is specific to the target substance can be acquired. Therefore, a sensor chip capable of specifying a target substance from a SERS spectrum by improving the sensitivity of the sensor can be provided. By appropriately changing the period and the height of the first protrusion, the height of the second protrusion, and the height of the third protrusion, the position of the resonant peak can be adjusted to an arbitrary wavelength. Accordingly, it is possible to appropriately select the wavelength of light that is emitted when specifying a target substance, whereby the width of the measurement range increases.

In the above-described sensor chip, it is preferable that the plurality of the first protrusions is periodically arranged in a second direction that intersects with the first direction and is parallel to the planar portion. In such a case, sensing can be performed under conditions of plasmon resonance that are broader than that of a case where the first protrusions are formed periodically only in the direction (the first direction) parallel to the planar portion of the substrate. Accordingly, a sensor chip capable of specifying a target substance from a SERS spectrum by improving the sensitivity of the sensor can be provided. Furthermore, in addition to the period of the first protrusions in the first direction, the period in the second direction can be appropriately changed. Accordingly, it is possible to appropriately select the wavelength of light that is emitted when specifying a target substance, whereby the width of the measurement range increases.

In the above-described sensor chip, it is preferable that the plurality of second protrusions and the plurality of third protrusions are periodically arranged in a third direction that is parallel to the planar portion. In such a case, the periods of the second protrusions and the third protrusions can be appropriately changed. Accordingly, it is possible to appropriately select the wavelength of light that is emitted when specifying a target substance, whereby the width of the measurement range increases.

In the above-described sensor chip, it is preferable that the plurality of second protrusions and the plurality of third protrusions are periodically arranged in a fourth direction that intersects with the third direction and is parallel to the planar portion. In such a case, sensing can be performed under conditions of plasmon resonance that are broader than that of a case where the second protrusions and the third protrusions are formed only in the direction (the third direction) parallel to the planar portion of the substrate. Accordingly, a sensor chip capable of specifying a target substance from a SERS spectrum by improving the sensitivity of the sensor can be provided. Furthermore, in addition to the periods of the second protrusions and the third protrusions in the third direction, the period in the fourth direction can be appropriately changed. Accordingly, it is possible to appropriately select the wavelength of light that is emitted when specifying a target substance, whereby the width of the measurement range increases.

In the above-described sensor chip, it is preferable that the plurality of second protrusions and the plurality of third protrusions are formed from fine particles. In such a case, a sensor chip capable of specifying a target substance from a SERS spectrum by improving the sensitivity of the sensor can be provided.

In the above-described sensor chip, it is preferable that the metal that composes the surface of the diffraction grating is gold or silver. In such a case, since gold or silver has characteristics for exhibiting the SPP, the LSPR, and the SERS, the SPP, the LSPR, and the SERS can be easily exhibited, whereby a target substance can be detected with high sensitivity.

According to a second aspect of the invention, there is provided a sensor cartridge including: the above-described sensor chip; a transport unit that transports the target substance to a surface of the sensor chip; a placement unit in which the sensor chip is placed; a casing that houses the sensor chip, the transport unit, and the placement unit; and an irradiation window that is disposed at a position facing the surface of the sensor chip on the casing.

According to the second aspect of the invention, since the above-described sensor chip is included, a target molecule can be detected by performing selective spectroscopy for the Raman scattering light. Therefore, a sensor cartridge capable of specifying a target substance from the SERS spectrum by improving the sensitivity of the sensor can be provided.

According to a third aspect of the invention, there is provided an analysis apparatus including: the above-described sensor chip; a light source that emits light to the sensor chip; and a photo detector that detects light scattered by the sensor chip.

According to the third aspect of the invention, since the above-described sensor chip is included, a target molecule can be detected by performing selective spectroscopy for the Raman scattering light. Therefore, an analysis apparatus capable of specifying a target substance from a SERS spectrum by improving the sensitivity of the sensor can be provided.

According to a fourth aspect of the invention, there is provided a sensor chip including: a substrate that has a planar portion; and a diffraction grating having a composite pattern in the planar portion and a metal surface, the diffraction grating having a target substance thereon and superimposedly including: a first protrusion pattern in which a plurality of first protrusions is periodically arranged in a period equal to or greater than 100 nm and equal to or less than 1000 nm, a second protrusion pattern in which a plurality of second protrusions is periodically arranged in the plurality of first protrusions in a period shorter than that of the first protrusion pattern and a third protrusion pattern in which a plurality of third protrusions is arranged periodically in a period shorter than that of the first protrusion pattern in a base portion of the substrate located between two adjacent first protrusions.

According to the fourth aspect of the invention, a proximal electric field that is enhanced through surface plasmon resonance by the first protrusion is excited toward the surface having the same shape, and surface enhanced Raman scattering (SERS) having a high degree of enhancement can be further exhibited by a metallic microstructure due to the second protrusion. More specifically, when light is incident to a face on which the first protrusion pattern and the second protrusion pattern are formed, a surface-specific oscillation mode (surface plasmon) is formed by the first protrusion pattern. Then, free electrons are in a state of resonant oscillation accompanying the oscillation of light, and accordingly, the oscillation of an electromagnetic wave is excited accompanying the oscillation of the free electrons. Since the oscillation of the free electrons is influenced by the oscillation of this electromagnetic wave, a system acquired by coupling the oscillations of both the parties, that is, a so-called surface plasmon polariton (SPP) is formed. Accordingly, localized surface plasmon resonance (LSPR) is excited near the second protrusion pattern. In this structure, since the distance between two of the second protrusions adjacent to each other is short, an extremely strong enhanced electric field is generated near the contact points thereof. Then, when one to several target substances are adsorbed on the contact points, the SERS occurs from the contact points. Accordingly, a sharp SERS spectrum that is specific to the target substance can be acquired. Therefore, a sensor chip capable of specifying a target substance from a SERS spectrum by improving the sensitivity of the sensor can be provided. By appropriately changing the period and the height of the first protrusion, the height of the second protrusion, and the height of the third protrusion, the position of the resonant peak can be adjusted to an arbitrary wavelength. Accordingly, it is possible to appropriately select the wavelength of light that is emitted when specifying a target substance, whereby the width of the measurement range increases.

In the above-described sensor chip, it is preferable that the plurality of first protrusions is periodically arranged in a first direction that is parallel to the planar portion and is periodically arranged in a second direction that intersects with the first direction and is parallel to the planar portion. In such a case, sensing can be performed under conditions of plasmon resonance that are broader than that of a case where the first protrusions are formed periodically only in the direction (the first direction) parallel to the planar portion of the substrate. Accordingly, a sensor chip capable of specifying a target substance from a SERS spectrum by improving the sensitivity of the sensor can be provided. Furthermore, in addition to the period of the first protrusions in the first direction, the period in the second direction can be appropriately changed. Accordingly, it is possible to appropriately select the wavelength of light that is emitted when specifying a target substance, whereby the width of the measurement range increases.

In the above-described sensor chip, it is preferable that the plurality of second protrusions and the plurality of third protrusions are periodically arranged in a third direction that is parallel to the planar portion. In such a case, the periods of the second protrusions and the third protrusions can be appropriately changed. Accordingly, it is possible to appropriately select the wavelength of light that is emitted when specifying a target substance, whereby the width of the measurement range increases.

In the above-described sensor chip, it is preferable that the plurality of second protrusions and the plurality of third protrusions are periodically arranged in a fourth direction that intersects with the third direction and is parallel to the planar portion. In such a case, sensing can be performed under conditions of plasmon resonance that are broader than that of a case where the second protrusions and the third protrusions are formed only in the direction (the third direction) parallel to the planar portion of the substrate. Accordingly, a sensor chip capable of specifying a target substance from a SERS spectrum by improving the sensitivity of the sensor can be provided. Furthermore, in addition to the periods of the second protrusions and the third protrusions in the third direction, the period in the fourth direction can be appropriately changed. Accordingly, it is possible to appropriately select the wavelength of light that is emitted when specifying a target substance, whereby the width of the measurement range increases.

In the above-described sensor chip, it is preferable that the plurality of second protrusions and the plurality of third protrusions are formed from fine particles. In such a case, a sensor chip capable of specifying a target substance from a SERS spectrum by improving the sensitivity of the sensor can be provided.

In the above-described sensor chip, it is preferable that the metal that composes the surface of the diffraction grating is gold or silver. In such a case, since gold or silver has a characteristic of exhibiting the SPP, the LSPR, and the SERS, the SPP, the LSPR, and the SERS can be easily exhibited, whereby a target substance can be detected with high sensitivity.

According to a fifth aspect of the invention, there is provided a sensor cartridge including: the above-described sensor chip; a transport unit that transports the target substance to a surface of the sensor chip; a placement unit in which the sensor chip is placed; a casing that houses the sensor chip, the transport unit, and the placement unit; and an irradiation window that is disposed at a position facing the surface of the sensor chip on the casing.

According to the fifth aspect of the invention, since the above-described sensor chip is included, a target molecule can be detected by performing selective spectroscopy for the Raman scattering light. Therefore, a sensor cartridge capable of specifying a target substance from the SERS spectrum by improving the sensitivity of the sensor can be provided.

According to a sixth aspect of the invention, there is provided an analysis apparatus including: the above-described sensor chip; a light source that emits light onto the sensor chip; and a photo detector that detects light scattered by the sensor chip.

According to the sixth aspect of the invention, since the above-described sensor chip is included, a target molecule can be detected by performing selective spectroscopy for the Raman scattering light. Therefore, an analysis apparatus capable of specifying a target substance from a SERS spectrum by improving the sensitivity of the sensor can be provided.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1A:
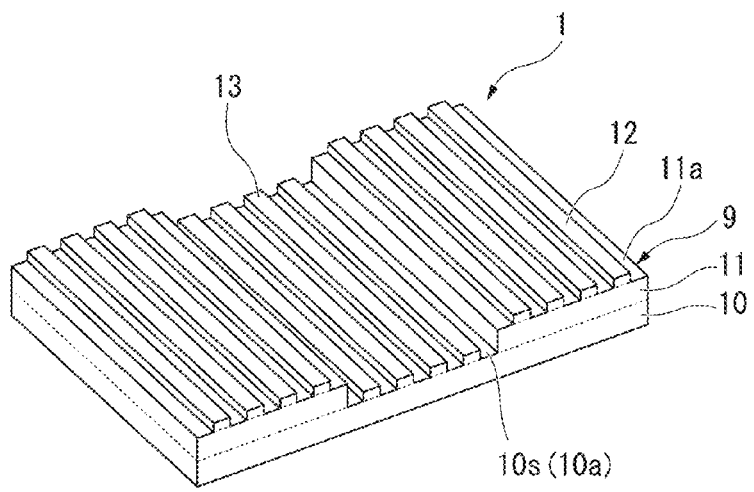
FIGS. 1A and 1B are schematic diagrams representing a schematic configuration of a sensor chip according to an embodiment of the invention.

Hereinafter, an embodiment of the invention will be described with reference to the accompanying drawings. Such an embodiment represents one aspect of the invention and is not for the purpose of limiting the invention. Thus, various changes can be arbitrarily made therein within the scope of the technical idea of the invention. In the drawings described below, for easy understanding of each configuration, the scales, the numbers, and the like of structures are different from those of the actual structures.

Figure 1B:
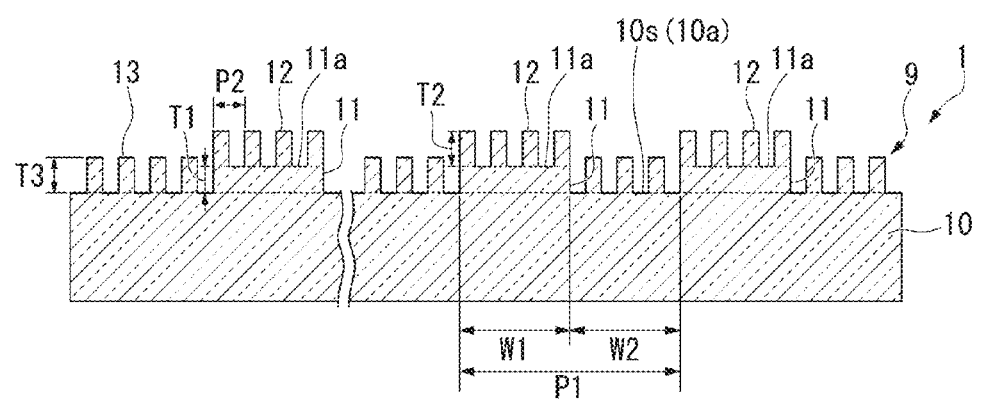

FIGS. 1A and 1B are schematic diagrams representing a schematic configuration of a sensor chip according to an embodiment of the invention. FIG. 1A is a perspective view of the sensor chip showing a schematic configuration thereof. FIG. 1B is a cross-sectional view of the sensor chip showing a schematic configuration thereof. In FIG. 1B, the reference sign P1 is a period of the first protrusion (the first convex shape), the reference sign P2 is a period of the second protrusion (the second convex shape) and the third protrusion (third convex shape), the reference sign T1 is the height of the first protrusion (the depth of the groove), the reference sign T2 is the height of the second protrusion (the depth of the groove), the reference sign T3 is the height of the third protrusion (the depth of the groove), the reference sign W1 represents the width of the first protrusion, and the reference sign W2 is the distance between two of the first protrusions that are adjacent to each other.

Figure 15:
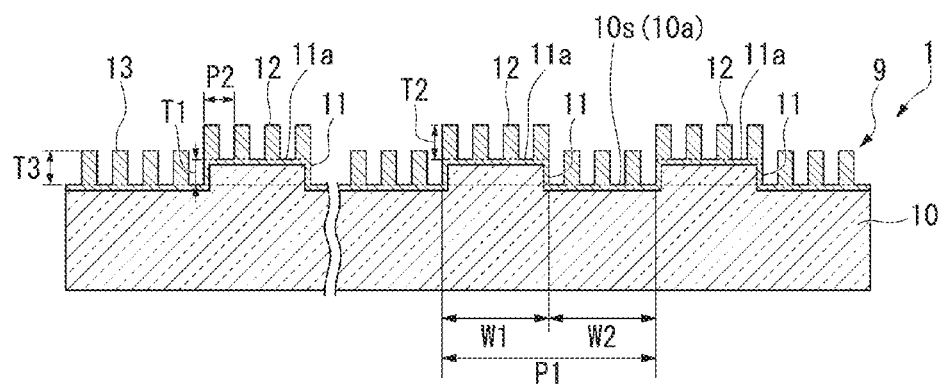
FIG. 15 is a schematic diagram showing a schematic configuration of a sensor chip according to an embodiment of the invention.
Figure 16:
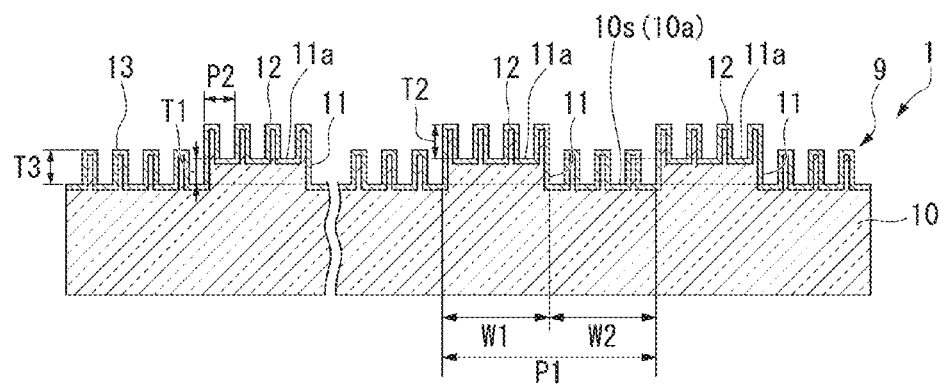
FIG. 16 is a schematic diagram showing a schematic configuration of a sensor chip according to an embodiment of the invention.

FIGS. 15 and 16 are schematic diagrams showing schematic configurations of sensor chips according to an embodiment of the invention, which correspond to FIG. 1B. In FIGS. 15 and 16, the reference sign P1 is a period of the first protrusion (the first convex shape), the reference sign P2 is a period of the second protrusion (the second convex shape) and the third protrusion (the third convex shape), the reference sign T1 is the height of the first protrusion (the depth of the groove), the reference sign T2 is the height of the second protrusion (the depth of the groove), the reference sign T3 is the height of the third protrusion (the depth of the groove), the reference sign W1 represents the width of the first protrusion, and the reference sign W2 is the distance between two of the first protrusions that are adjacent to each other.

The sensor chip 1 is used for placing a target substance in a diffraction grating 9 that is formed in a substrate 10 containing metal and detecting the target substance by using localized surface Plasmon resonance (LSPR) and surface enhanced Raman scattering (SERS).

The diffraction grating 9 includes: a plurality of the first protrusions 11 that is arranged in a period P1 equal to or greater than 100 nm and equal to or less than 1000 nm in the first direction that is parallel to a planar portion of the substrate 10; a plurality of base portions 10a that is positioned between two of the first protrusions 11 adjacent to each other and configures the base of the substrate 10; a plurality of the second protrusions 12 that is formed on an upper face 11a of each of the plurality of the first protrusions 11; and a plurality of the third protrusions 13 that is formed on each of the plurality of the base portions 10a. The diffraction grating 9 has a surface formed from a metal and is formed on a planar portion 10s of the substrate 10.

In other words, the diffraction grating 9 has a composite pattern acquired by superimposing the first protrusion pattern in which a plurality of the first protrusions (the first convex shapes) 11 is arranged in a period P1 equal to or greater than 100 nm and equal to or less than 1000 nm in a direction perpendicular to the planar portion of the substrate 10, the second protrusion pattern in which a plurality of the second protrusions (the second convex shapes) 12 is arranged periodically in a period P2 shorter than that of the first protrusion pattern in each of the plurality of the first protrusions 11, and the third protrusion pattern in which a plurality of the third protrusions is arranged in a period P2 shorter than that of the first protrusion pattern in the base portion located between two of the first protrusions 11 adjacent to each other, and has a surface formed from a metal. And the protrusions could also have a rounded/convex shape rather than the rectangular shape shown in the drawings.

The "diffraction grating" described here represents a structure in which a plurality of protrusion patterns (a plurality of protrusions) is periodically arranged.

In addition, the "planar portion" described here represents an upper face portion of the substrate. In other words, the "planar portion" represents one surface portion of the substrate on which a target substance is placed. The composite pattern that is formed by superimposing the first protrusion pattern, the second protrusion pattern, and the third protrusion pattern together is formed on at least the upper face portion of the substrate. The shape of the other surface portion, that is, a lower face portion of the substrate is not particularly limited. However, in consideration of the processing process or the like performed for the planar portion (the upper face portion) of the substrate, it is preferable that the lower face portion of the substrate is parallel to the base portion of the planar portion and is a flat face.

As an example of the configuration of the diffraction grating 9, as shown in FIG. 1B, there is a structure in which the substrate 10, the first protrusion 11, and the second protrusion 12 are all formed from metal. In addition, as shown in FIG. 15, there is a structure in which the substrate 10 and the first protrusion 11 are formed by an insulating member formed from glass, resin, or the like, all the exposed portions of the insulating member are covered with a metal film, and the second protrusion 12 formed from a metal is formed on the metal film, and the third protrusion 13 formed from a metal is formed. In addition, as shown in FIG. 16, there is a structure in which all the substrate 10, the first protrusion 11, the second protrusion 12, and the third protrusion 13 are formed by an insulating member, and all the exposed portions of the insulating member are covered with a metal film. In other words, the diffraction grating 9 has a configuration in which the base portion 10a of the substrate 10 and at least the surfaces of the first protrusion 11, the second protrusion 12, and the third protrusion 13 are formed from a metal.

The substrate 10, for example, has a structure in which a metal film having a thickness of 150 nm or more is formed on a glass substrate. This metal film becomes the first protrusion 11, the second protrusion 12, and the third protrusion 13 through a manufacturing process to be described later. In this embodiment, as the substrate 10, a substrate in which a metal film is formed on the glass substrate is used. However, the substrate 10 is not limited thereto. For example, a substrate in which a metal film is formed on a quartz substrate or sapphire substrate may be used as the substrate 10. In addition, a flat plate formed from metal may be used as the substrate.

The first protrusions 11 are formed on the planar portion 10s of the substrate 10 so as to have a predetermined height T1. These first protrusions 11 are arranged in a period P1 that is shorter than the wavelength of light in a direction (the first direction) parallel to the planar portion 10s of the substrate 10. In the period P1, the width of a single body of the first protrusion 11 in the first direction (the horizontal direction in FIG. 1B) and the distance between two of the first protrusions 11 that are adjacent to each other are added together. In addition, the first protrusion 11 is in a rectangular convex shape in the cross-sectional view, and a plurality of the first protrusions 11 is formed in a line and space (a stripe shape) in the plan view.

It is preferable that, for example, the period P1 of the first protrusions 11 is set in the range of 100 nm to 1000 nm, and the height T1 of the first protrusions 11 is set in the range of 10 nm to 100 nm. Accordingly, the first protrusions 11 can serve as a structure for exhibiting the LSPR.

The width W1 of the first protrusion 11 in the first direction is greater than the distance W2 between two of the first protrusions 11 that are adjacent to each other (W1>W2). Accordingly, the spatial filling rate of the first protrusions 11 in which the LSPR is excited increases.

Two or more second protrusions 12 are formed on the upper face 11a of each of the plurality of the first protrusions 11 so as to have a predetermined height T2. In addition, two or more third protrusions 13 are formed on each of the plurality of the base portions 10a so as to have a predetermined height T3.

The second protrusions 12 and the third protrusions 13 are arranged in a period P2 that is shorter than the wavelength of light in a direction (the third direction) parallel to the planar portion 10s of the substrate 10. In the period P2, the width of a single body of the second protrusion 12 in the third direction (the horizontal direction in FIG. 1B) and the distance between two of the second protrusions 12 that are adjacent to each other are added together (the width of the single body of the third protrusion 13 in the third direction and the distance between two of the third protrusions 13 adjacent to each other are added together). Accordingly, the period P2 of the second protrusions 12 (the third protrusion 13) is sufficiently shorter than that P1 of the first protrusions 11.

It is preferable that, for example, the period P2 of the second protrusions 12 and the third protrusions 13 is set to a value less than 500 nm, and the heights T2 and T3 of the second and third protrusions 12 and 13 are set to a value less than 200 nm. Accordingly, the second protrusions 12 and the third protrusions 13 can serve as a structure for exhibiting the SERS.

In this embodiment, the arrangement direction (the first direction) of the first protrusions 11 and the arrangement direction (the third direction) of the second protrusions 12 and the third protrusions 13 are the same. In addition, second protrusion 12 and the third protrusion 13 are in a rectangular convex shape in the cross-sectional view, and a plurality of the second protrusions 12 and a plurality of the third protrusions 13 are formed in a line and space (a stripe shape) in the plan view.

As metal of the surface of the diffraction grating 9, for example, gold (Au), silver (Ag), copper (Cu), aluminum (Al), or an alloy thereof is used. In this embodiment, Au or Ag that has a characteristic of exhibiting the SPP, the LSPR, and the SERS is used. Accordingly, the SPP, the LSPR, and the SERS can be easily exhibited, and a target substance can be detected with high sensitivity.

Here, the LSPR, and the SERS will be described. When light is incident to the surface of the sensor chip 1, that is, the face on which the plurality of the first protrusions 11, the plurality of the second protrusions 12, and the plurality of the third protrusions 13 are formed, a surface-specific oscillation mode (surface plasmon) is formed by the plurality of the first protrusions 11. However, the polarizing direction of the incident light is perpendicular to the groove direction of the first protrusions 11. Then, the oscillation of an electromagnetic wave is excited accompanied by the oscillation of free electrons. Since the oscillation of the free electrons is influenced by this oscillation of the electromagnetic wave, a system acquired by coupling both the oscillations, that is, a so-called surface plasmon polariton (SPP) is formed. In this embodiment, the incident angle of light is approximately vertical with respect to the surface of the sensor chip 1. However, the incident angle is not limited to this angle (vertical), as long as it satisfies a condition for exciting the SPP.

This SPP propagates along the surface of the sensor chip 1, and more specifically, along an interface between the air and the second and third protrusions 12 and 13 and excites a strong localized electric field near the second protrusion 12 and the third protrusion 13. The coupling of the SPP is sensitive to the wavelength of light, and the coupling efficiency is high. As described above, localized surface plasmon resonance (LSPR) can be excited from the incident light that is in the air propagation mode through the SPP. Then, from the relationship between the LSPR and Raman scattering light, surface enhanced Raman scattering (SERS) can be used.

Figure 2A:
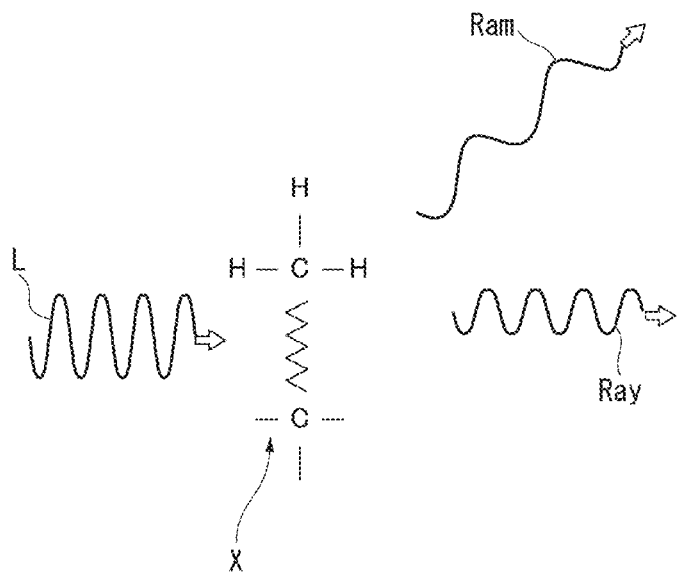
FIGS. 2A and 2B are diagrams representing a Raman scattering spectroscopy.
Figure 2B:
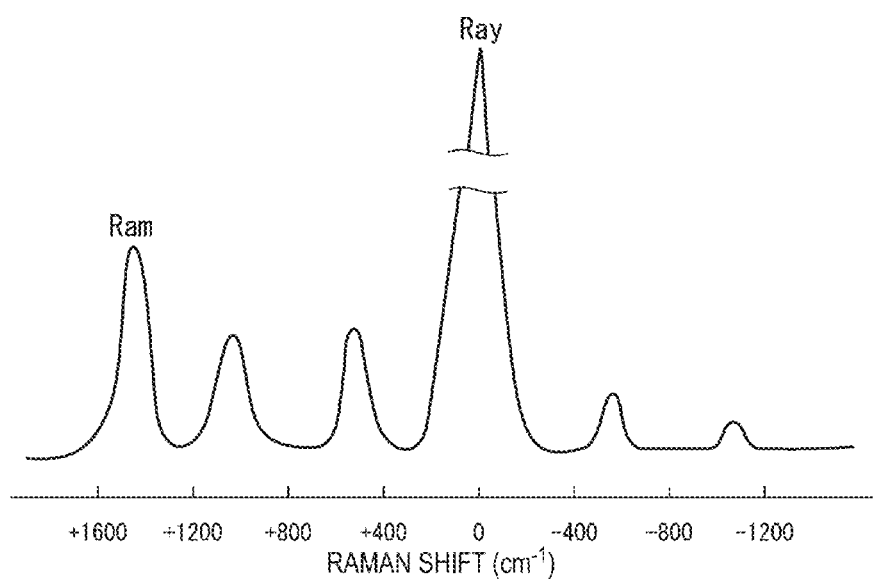

FIGS. 2A and 2B are diagrams representing a Raman scattering spectroscopy. FIG. 2A represents the principle of the Raman scattering spectroscopy. In addition, FIG. 2B represents a Raman spectrum (the relationship between a Raman shift and the intensity of Raman scattering). In FIG. 2A, the reference sign L represents incident light (light of a single wavelength), the reference sign Ram represents Raman scattering light, the reference sign Ray represents Rayleigh scattering light, and the reference sign X represents a target molecule (target substance). In FIG. 2B, the horizontal axis represents the Raman shift. Here, the Raman shift is the difference between the frequency of the Raman scattering light Ram and the frequency of the incident light L and has a value that is specific to the structure of the target molecule X.

As shown in FIG. 2A, when light L of a single wavelength is emitted to the target molecule X, light having a wavelength different from that of the incident light is generated in the scattering light (Raman scattering light Ram). The difference between the energy levels of the Raman scattering light Ram and the incident light L corresponds to the energy of the oscillation level, the rotation level, or the electron levels of the target molecule X. The target molecule X has an oscillation energy level that is specific to the structure thereof, and accordingly, the target molecule X can be specified by using the light L of a single wavelength.

For example, when the oscillation energy of the incident light L is denoted by V1, the oscillation energy consumed by the target molecule X is denoted by V2, and the oscillation energy of the Raman scattering light Ram is denoted by V3, $V3=V1-V2$. After colliding with the target molecule X, most of the incident light L has energy with the same magnitude as that of energy before the collision. This elastic scattering light is termed Rayleigh scattering light Ray. For example, when the oscillation energy of the Rayleigh scattering light Ray is denoted by V4, $V4=V1$.

From the Raman spectrum shown in FIG. 2B, it can be known that the Raman scattering light Ram is weak by comparing the scattering intensity (spectrum peak) of the Raman scattering light Ram and the scattering intensity of the Rayleigh scattering light Ray. As described above, the Raman scattering spectroscopy is a measurement technique that has a superior capability for identifying a target molecule X and a low sensitivity for sensing a target molecule X. Accordingly, in this embodiment, in order to increase the sensitivity, spectroscopy using the surface enhanced Raman scattering (SERS spectroscopy) is used (see FIG. 4).

Figure 3A:
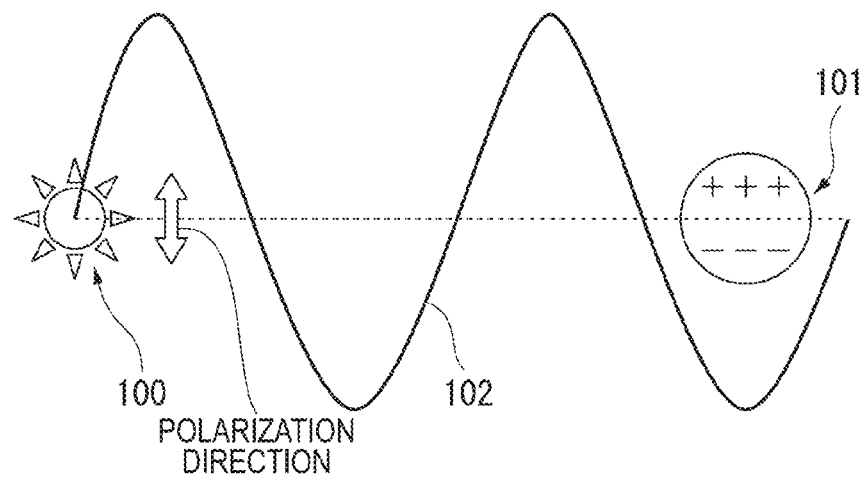
FIGS. 3A and 3B are diagrams representing an electric field enhancing mechanism using LSPR.
Figure 3B:
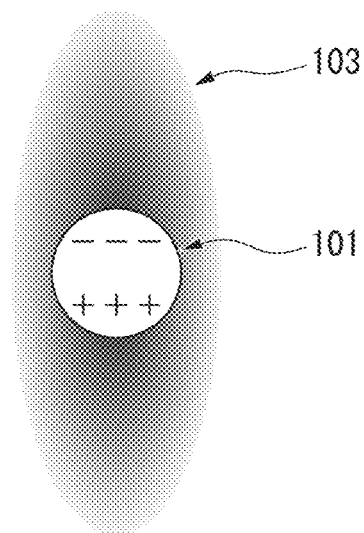

FIGS. 3A and 3B are diagrams representing an electric field enhancing mechanism using the LSPR. FIG. 3A is a schematic diagram representing a state when light is incident to a metal nanoparticle. FIG. 3B is a diagram representing an LSPR enhanced electric field. In FIG. 3A, the reference sign 100 represents a light source, the reference sign 101 represents a metal nanoparticle, and the reference sign 102 represents light emitted from the light source. In FIG. 3B, the reference sign 103 represents a surface localized electric field.

As shown in FIG. 3A, when the light 102 is incident to the metal nanoparticle 101, free electrons are in a state of resonant oscillation accompanying the oscillation of the light 102. The particle diameter of the metal nanoparticle is smaller than the wavelength of the incident light. For example, the wavelength of the light is in the range of 400 nm to 800 nm, and the particle diameter of the metal nanoparticle is in the range of 10 nm to 100 nm. As the metal nanoparticle, Ag or Au is used.

Then, a strong surface localized electric field 103 is excited near the metal nanoparticle 101 accompanying the resonant oscillation of the free electrons (see FIG. 3B). As above, the LSPR can be excited by allowing the light 102 to be incident to the metal nanoparticle 101.

Figure 4:
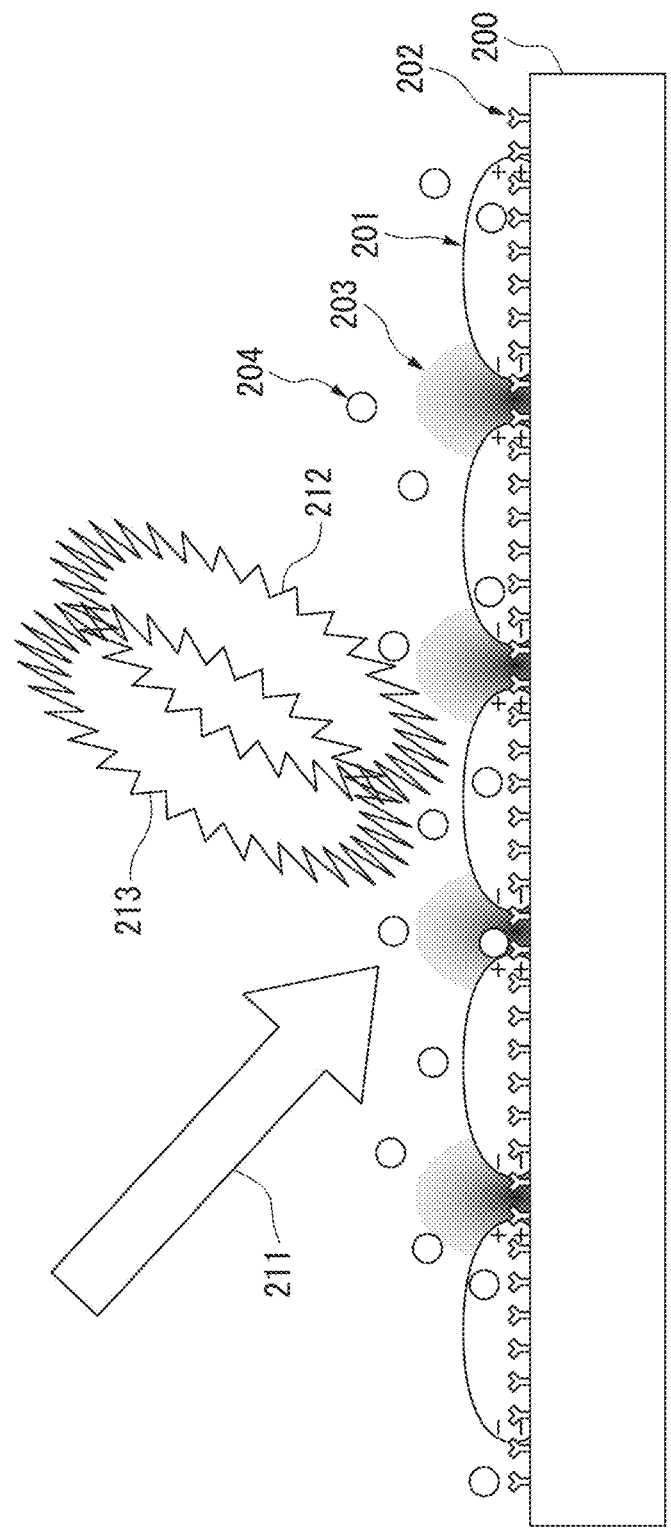
FIG. 4 is a diagram representing the SERS spectroscopy.

FIG. 4 is a diagram representing the SERS spectroscopy. In FIG. 4, the reference sign 200 represents a substrate, the reference sign 201 represents a metal nanostructure, the reference sign 202 represents a selective adsorption film, the reference sign 203 represents an enhanced electric field, the reference sign 204 represents a target molecule, the reference sign 211 represents an incident laser beam, the reference sign 212 represents Raman scattering light, and the reference sign 213 represents Rayleigh scattering light. The selective adsorption film 202 adsorbs the target molecule 204.

As shown in FIG. 4, when the laser beam 211 is incident to the metal nanostructure 201, free electrons are in a state of resonant oscillation accompanying the oscillation of the laser beam 211. The size of the metal nanostructure 201 is smaller than the wavelength of the incident laser beam. Then, accompanying the resonant oscillation of the free electrons, a strong surface localized electric field is excited near the metal nanostructure 201. Accordingly, the LSPR is excited. When the distance between the metal nanostructures 201 that are adjacent to each other decreases, an extremely strong enhanced electric field 203 is generated near the contact point. When one to several target molecules 204 are adsorbed on the contact points, the SERS occurs from the contact points. This point is also checked by the result of an enhanced electric field generated between two adjacent silver nanoparticles that is calculated by using a finite difference time domain (FDTD) method. Accordingly, by performing selective spectroscopy for the Raman scattering light, the target molecule can be detected with high sensitivity.

This embodiment, as described above, has a structure in which the LSPR is excited by arranging the first protrusions 11 in the period P1 shorter than the wavelength of the light in the direction parallel to the planar portion of the substrate 10. In addition, this embodiment has a structure in which the SERS is exhibited by forming two or more of the second protrusions 12 on the upper face 11a of the first protrusion 11 and forming two or more of the third protrusions 13 on the base portion 10a. More specifically, when light of a single wavelength is emitted to a target molecule, based on the principle of generating the Raman scattering light, an enhanced magnetic field is generated near the contact point by disposing the target molecules between two of the second protrusions 12 (the third protrusions 13) that are adjacent to each other, whereby the SERS occurs. Accordingly, it is possible to use the SERS spectroscopy capable of detecting a target substance with sensitivity that is higher than that of the Raman scattering spectroscopy.

Figure 5:
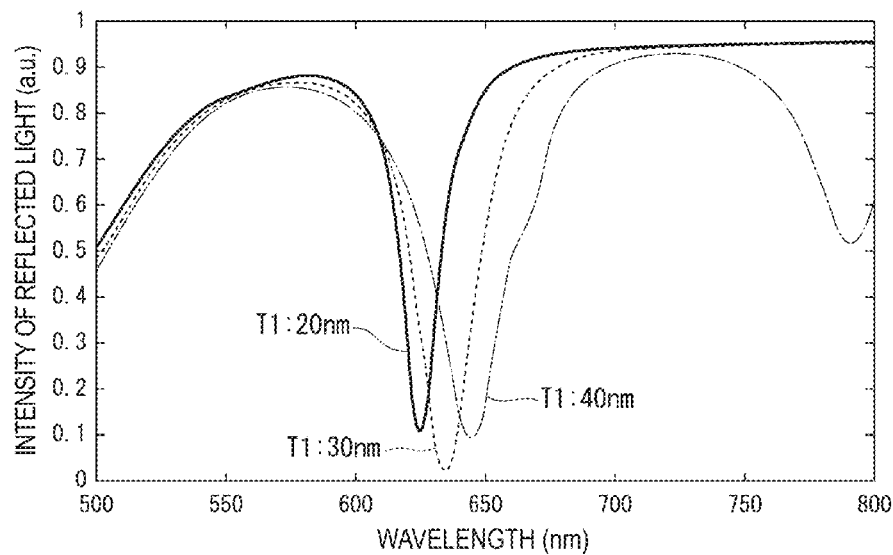
FIG. 5 is a graph representing the intensity of reflected light reflected from a single body of the first protrusion.

FIG. 5 is a graph representing the intensity of reflected light reflected from a single body of the first protrusion. In FIG. 5, the horizontal axis represents the wavelength of light, and the vertical axis represents the intensity of the reflected light. The height T1 of the first protrusion 11 is taken as a parameter (T1=20 nm, 30 nm, and 40 nm). In addition, in the structure of the sensor chip 1 according to this embodiment, a value calculated by subtracting the intensity of the reflected light from the intensity of the incident light (assumed to be 1.0) is absorbance.

The light is incident vertically to the first protrusion 11. Regarding the polarization directions of the light, there are polarized light having an electric field component parallel to the groove (the extending direction of an area between the first protrusions 11 adjacent to each other) and TM (Transverse Magnetic) polarized light having an electric field component perpendicular thereto. The period of the first protrusions 11 is 580 nm, and the resonant peak of the intensity of the reflected light is near a wavelength 630 nm. This resonant peak originates from the SPP, and as the height T1 of the first protrusion 11 is increased, the resonant peak is shifted to the long wavelength side (the long wavelength region). When the height T1 of the first protrusion 11 is 30 nm, the intensity of the reflected light is the highest, and accordingly, it can be known that absorption is represented to be the strongest.

Figure 6:
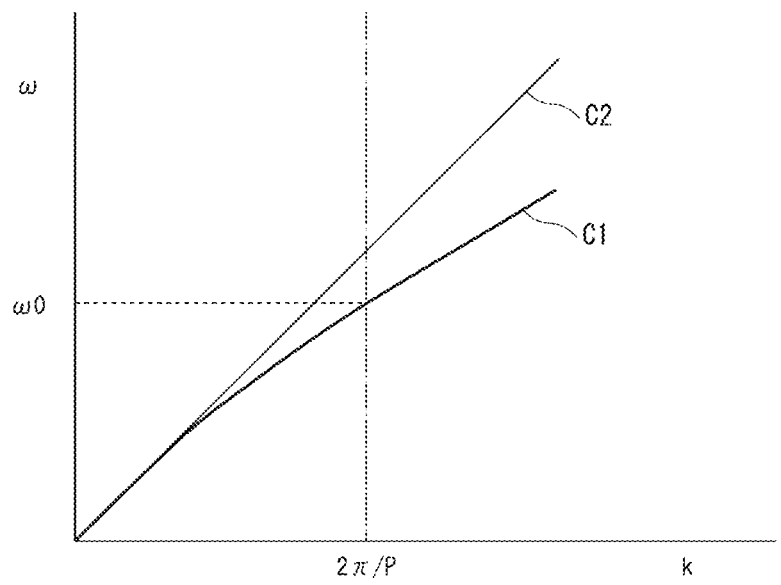
FIG. 6 is a graph representing the dispersion curve of SPP.

FIG. 6 is a graph representing the dispersion curve of the SPP. In FIG. 6, the reference sign C1 represents a dispersion curve (as an example, it represents a value at the interface of the air and Au) of the SPP, and the reference sign C2 represents a light line. The period of the first protrusion 11 is 580 nm. The position of the lattice vector of the first protrusion 11 is shown on the horizontal axis (corresponding to $2\pi/P$ on the horizontal axis shown in FIG. 6). When a line extends from this position toward the upper side, the line intersects with the dispersion curve of the SPP. The wavelength corresponding to this intersection is acquired by using the following equation.

$$\lambda = P1\sqrt{[(E1 \cdot E2)/(E1+E2)]} \quad (1)$$

In Equation (1), P1 represents the period of the first protrusions 11, E1 represents the complex permittivity of the air, and E2 represents the complex permittivity of Au. By substituting P1, E1, and E2 with respective values in Equation (1), $\lambda=620$ nm is acquired (corresponding to w0 on the vertical axis shown in FIG. 6).

As the height T1 of the first protrusion 11 is increased, the imaginary part of the wave number of the SPP increases. Accordingly, the real part of the wave number of the SPP decreases, whereby the intersection of the line extended from the position of the lattice vector and the dispersion curve of the SPP moves from the upper right side to the lower left side. In other words, the resonant peak is shifted to the long wavelength side.

Figure 7:
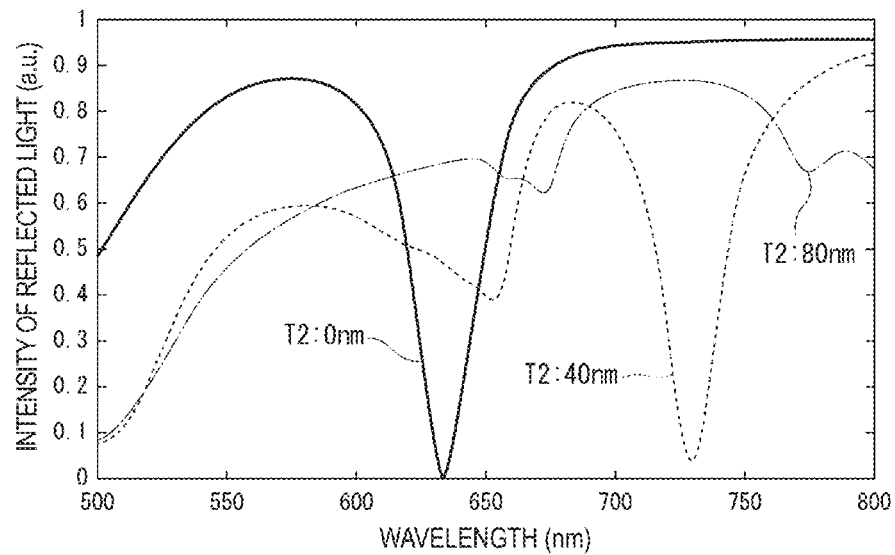
FIG. 7 is a graph representing the intensity of reflected light of a sensor chip according to an embodiment of the invention.

FIG. 7 is a graph representing the intensity of reflected light of a structure in which the first protrusion 11 and the second protrusion 12 (the third protrusion 13) are superimposed with each other, that is, the sensor chip 1 according to the embodiment of the invention. In FIG. 7, the horizontal axis represents the wavelength of light, and the vertical axis represents the intensity of the reflected light. The height T2 of the second protrusion 12 (the height T3 of the third protrusion 13) is taken as a parameter (T2 (T3)=0 nm, 40 nm, and 80 nm). In addition, the graph of the parameter T2=0 in this figure is the same as the graph of the parameter T1=30 shown in FIG. 5.

The light is incident vertically to the first protrusion 11. The height T1 of the first protrusion 11 is 30 nm. In addition, the period P2 of the second protrusion 12 (the third protrusion 13) is 97 nm. The resonant peak of the intensity of the reflected light is near a wavelength 730 nm. Compared to the spectrum represented in JP-A-2000-356587, the width of the resonant peak is narrowed and sharpened. This resonant peak originates from the above-described SPP, and by superimposing the second protrusion 12 (the third protrusion 13) on the first protrusion 11, the position of the resonant peak is shifted to the long wavelength side. At this time, the sharpness and the gradient of the resonant peak are maintained. In a case where the height T2 (the height of the third protrusion 13) of the second protrusion 12 is 40 nm, a strong localized electric field can be excited near the surface of the second protrusion 12 by emitting light having a wavelength of 730 nm. In addition, by appropriately changing the periods P1 and P2 and the heights T1 and T2 (T3) of the first protrusion 11 and the second protrusion 12 (the third protrusion 13), the position of the resonant peak can be adjusted to an arbitrary wavelength.

Figure 8:
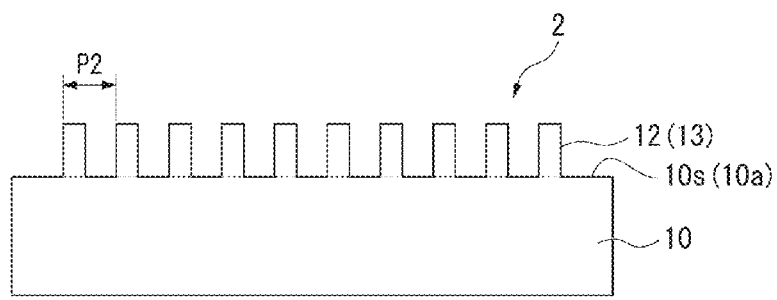
FIG. 8 is a schematic diagram of a sensor chip in which a plurality of the second protrusions is formed on the planar portion of the substrate.

FIG. 8 is a diagram schematically showing the sensor chip 2 in a case where the first protrusion 11 is not formed in the planar portion 10s of the substrate 10, and only the second protrusions 12 (the third protrusions 13) are formed on the planar portion 10s of the substrate 10, that is, a case where a plurality of the second protrusions 12 (the third protrusions 13) is formed on the planar portion 10s of the substrate 10.

Figure 9:
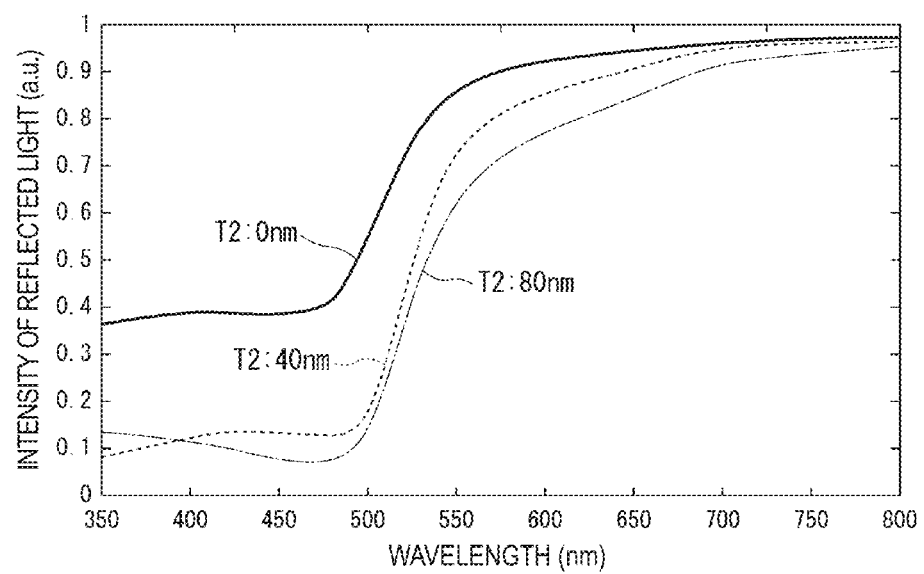
FIG. 9 is a graph representing the intensity of reflected light of a sensor chip shown in FIG. 8.

FIG. 9 is a graph representing the intensity of reflected light of a sensor chip 2 in a case where a plurality of the second protrusions 12 (the third protrusions 13) is formed on the planar portion 10s of the substrate 10. In FIG. 9, the horizontal axis represents the wavelength of light, and the vertical axis represents the intensity of the reflected light. The height T2 of the second protrusion 12 (the height T3 of the third protrusion 13) is taken as a parameter (T2 (T3)=0 nm, 40 nm, and 80 nm). The TM polarized light is incident vertically to the second protrusion 12 (the third protrusion 13). By referring to figure, a deep resonant peak of the intensity of the reflected light is not recognized. From this result, it can be known that light energy can hardly be coupled with the second protrusion 12 (the third protrusion 13) in a case where there is no first protrusion 11, that is, not through the SPP.

FIGS. 10A to 10F are diagrams representing the manufacturing process of the sensor chip. First, an Au film 31 is formed on a glass substrate 30 by using a method such as a deposition method or a sputtering method. Next, the upper face of the Au film 31 is coated with a resist 32 by using a method such as a spin coat method (see FIG. 10A). At this time, the Au film 31 is formed so as to have a film thickness Ta thick enough to not transmit incident light (for example, 100 nm).

Figure 10A:
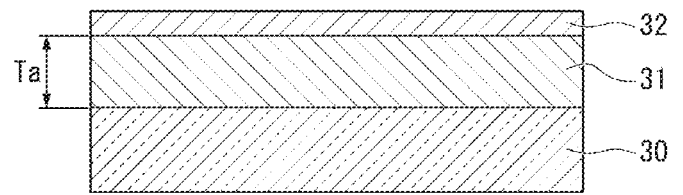
FIGS. 10A to 10F are diagrams representing the manufacturing process of the sensor chip.
Figure 10B:
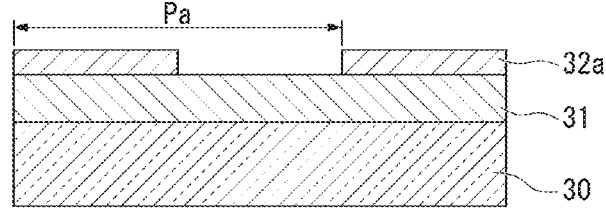
Figure 10C:
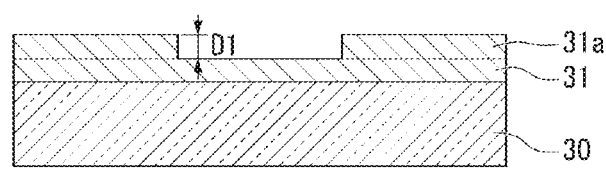

Next, a resist pattern 32a is formed in a period Pa of 580 nm by using a method such as an imprint method (see FIG. 10B). Next, the Au film 31 is etched to a predetermined depth D1 (for example, 30 nm) by performing dry etching by using the resist pattern 32a as a mask. Thereafter, by removing the resist pattern 32a, the first protrusion 31a is formed (see FIG. 10C).

Figure 10D:
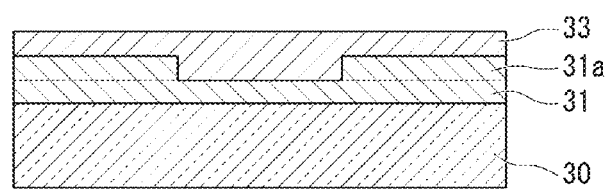
Figure 10E:
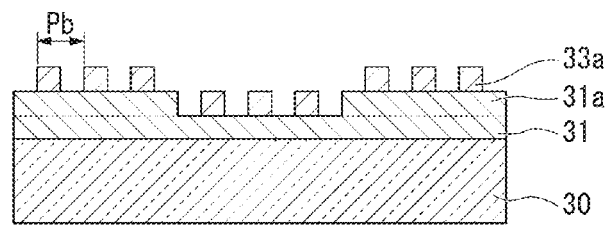
Figure 10F:
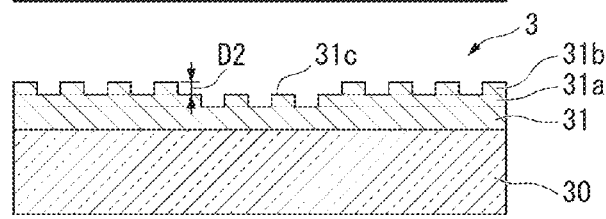

Next, the upper face of the Au film 31 on which the first protrusion 31a is formed is coated with a resist 33 by using a method such as a spin coat method (see FIG. 10D). Next, resist patterns 33a is formed in a period Pb of 97 nm by using a method such as an imprint method (see FIG. 10E). Next, the Au film 31 on which the first protrusion 31a is formed by dry etching is etched to a predetermined depth D2 (for example, 40 nm) by using the resist patterns 33a as a mask. Thereafter, the second protrusion 31b and the third protrusion 31c are formed by removing the resist patterns 33a (see FIG. 10F). By performing the above-described processes, a sensor chip 3 according to an embodiment of the invention can be manufactured.

In the sensor chip 1 according to the embodiment of the invention, the LSPR is excited through the SPP by a metallic microstructure due to the first protrusion 11, and the SERS can be further exhibited by a metallic microstructure due to the second protrusion 12 and the third protrusion 13. More specifically, when light is incident to a face on which a plurality of the first protrusions 11, a plurality of the second protrusions 12, and a plurality of the third protrusions 13 are formed, a surface-specific oscillation mode (surface plasmon) is formed by the plurality of the first protrusions 11. Then, free electrons are in a state of resonant oscillation due to oscillation of the light so as to excite the SPP, whereby a strong surface localized electric field is excited near the second protrusion 12 and the third protrusion 13. Accordingly, the LSPR is excited. In this structure, since the distance between two of the second protrusions 12 (the third protrusions 13) adjacent to each other is short, an extremely strong enhanced electric field is generated near contact points. Then, when one to several target substances are adsorbed on the contact points, the SERS occurs from the contact points. Accordingly, intensity characteristics in which the spectrum width of the intensity of the reflected light is small and the resonant peak is sharp can be acquired, whereby the sensitivity of the sensor can be improved. Therefore, a sensor chip 1 capable of specifying a target substance from the SERS spectrum by improving the sensitivity of the sensor can be provided. By appropriately changing the period P1 and the height T1 of the first protrusion 11, the height T2 of the second protrusion 12, and the height T3 of the third protrusion 13, the position of the resonant peak can be adjusted to an arbitrary wavelength. Accordingly, it is possible to appropriately select the wavelength of light that is emitted when specifying a target substance, whereby the width of the measurement range increases.

In addition, according to this configuration, since the second protrusions 12 and the third protrusions 13 are disposed periodically in the third direction parallel to the planar portion of the substrate 10, the period P2 of the second protrusions 12 and the third protrusions 13 can be appropriately changed. Accordingly, it is possible to appropriately select the wavelength of light that is emitted when specifying a target substance, whereby the width of the measurement range increases.

In addition, according to this configuration, gold or silver is used as the metal of the surface of the diffraction grating 9, and accordingly, the SPP, the LSPR and the SERS can be easily exhibited. Therefore, a target substance can be detected with high sensitivity.

In addition, according to this configuration, the duty ratio of the first protrusion 11 satisfies the relationship of "W1>W2", and accordingly, the spatial filling rate of the first protrusion 11 in which the LSPR is excited increases. Therefore, sensing can be performed under conditions of plasmon resonance that are broader than that of a case where the relationship of "W1<W2" is satisfied. In addition, the energy of light emitted when specifying a target substance can be effectively used.

In this embodiment, a structure in which the first protrusions 11 are arranged in the period P1 shorter than the wavelength of light in the direction (the first direction) parallel to the planar portion of the substrate 10 is represented. However, the invention is not limited thereto. A sensor chip 4 that has a structure of the first protrusion that is different from that of the first protrusion 11 according to this embodiment will be described with reference to FIG. 11.

Figure 11:
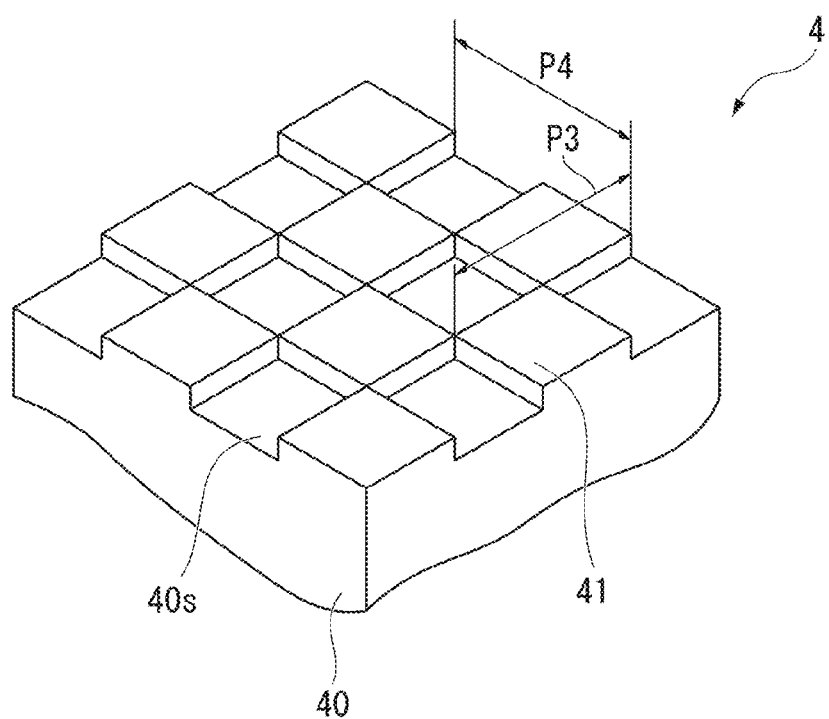
FIG. 11 is a schematic configuration diagram of a modified example of a sensor chip having the first protrusions.

FIG. 11 is a schematic perspective view showing the configuration of a sensor chip 4 that has the first protrusions 41 in a form different from that of the above-described first protrusions 11. In this figure, for convenience of description, the second protrusion and the third protrusion are not shown.

As shown in FIG. 11, the first protrusion 41 is formed on the planar portion 40s of a substrate 40. The first protrusions 41 are arranged in a period P3 shorter than the wavelength of the light in a direction (the first direction) parallel to the planar portion of the substrate 40. In addition, the first protrusions 41 are arranged in a period P4 that is shorter than the wavelength of the light in a second direction that is perpendicular to the first direction and is parallel to the planar portion of the substrate 40. Here, the second direction is not limited to a direction that is perpendicular to the first direction and is parallel to the planar portion of the substrate 40 and may be a direction that intersects with the first direction and is parallel to the planar portion of the substrate 40.

According to this structure, the SPP can be excited under conditions of resonance that are broader than that of a case where the first protrusions are formed only in the direction (the first direction) parallel to the planar portion of the substrate 10. Accordingly, a sensor chip 4 capable of specifying a target substance from the SERS spectrum by improving the sensitivity of the sensor can be provided. Furthermore, in addition to the period P3 of the first protrusions in the first direction, the period P4 in the second direction can be appropriately changed. Accordingly, the wavelength of the light emitted when specifying a target substance can be appropriately selected, whereby the width of the measurement range increases.

In this embodiment, a structure in which the second protrusions 12 and the third protrusions 13 are arranged in the period P2 shorter than the wavelength of the light in the direction (the third direction) parallel to the planar portion of the substrate 10, and more specifically, a structure in which the arrangement direction (the first direction) of the first protrusions 11 and the arrangement direction (the third direction) of the second protrusions 12 and the third protrusions 13 are the same direction is represented. However, the invention is not limited thereto. Thus, sensor chips 5, 6, 7, and 8 having a structure of the second protrusions and the third protrusions that is different from that of the second protrusion 12 and the third protrusions 13 according to this embodiment will be described with reference to FIGS. 12A to 13B.

Figure 12A:
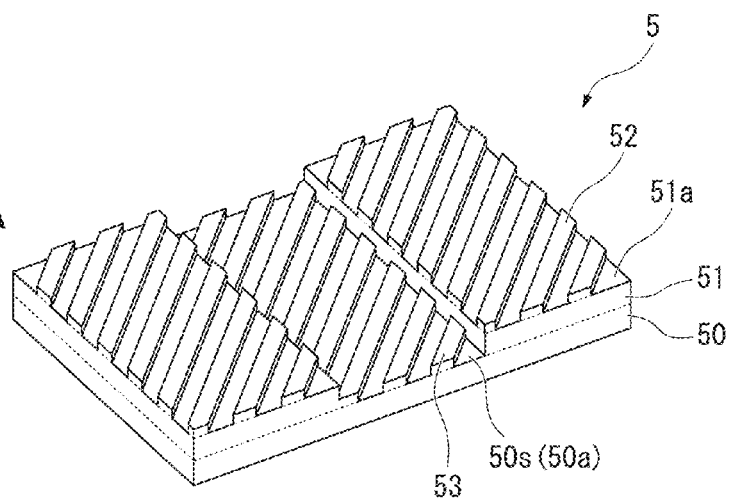
FIGS. 12A and 12B are schematic configuration diagrams showing modified examples of a sensor chip having the second protrusions.
Figure 12B:
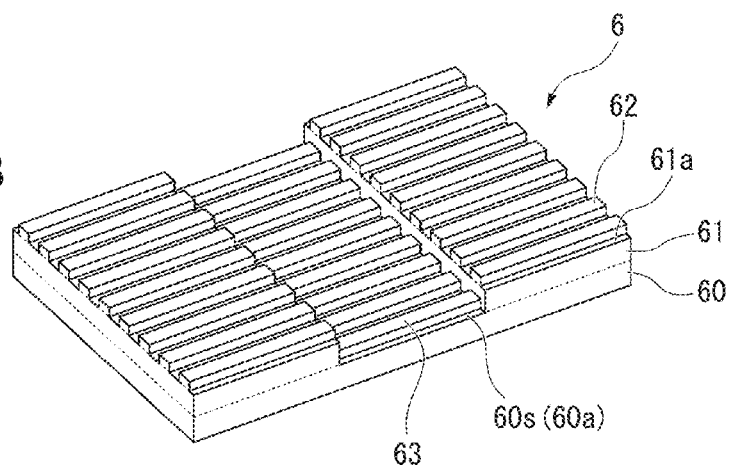

FIGS. 12A and 12B are schematic perspective views showing the configurations of sensor chips having the second protrusion and the third protrusion different from the above-described second protrusion 12 and the third protrusion 13 in the form. FIG. 12A is a sensor chip 5 that has the second protrusion 52 and the third protrusion 53. FIG. 12B is a sensor chip 6 that has the second protrusion 62 and the third protrusion 63.

As shown in FIG. 12A, two or more of the second protrusions 52 are formed on the upper face 51a of each of a plurality of the first protrusions 51. Two or more of the third protrusions 53 are formed on each of a plurality of the base portions 50a. In the figure, as an example, a structure in which the intersection angle of the arrangement direction (the first direction) of the first protrusions 51 and the arrangement direction (the third direction) of the second protrusions 52 and the third protrusions 53 is 45 degrees is represented.

As shown in FIG. 12B, two or more of the second protrusions 62 are formed on the upper face 61a of each of the plurality of the first protrusions 61. Two or more of the third protrusion 63 are formed on each of the plurality of the base portions 60a. In the figure, as an example, a structure in which the intersection angle of the arrangement direction (the first direction) of the first protrusions 61 and the arrangement direction (the third direction) of the second protrusions 62 and the third protrusions 63 is 90 degrees is represented.

According to this configuration, a sensor chip capable of specifying a target substance from the SERS spectrum by improving the sensitivity of the sensor can be provided.

Figure 13A:
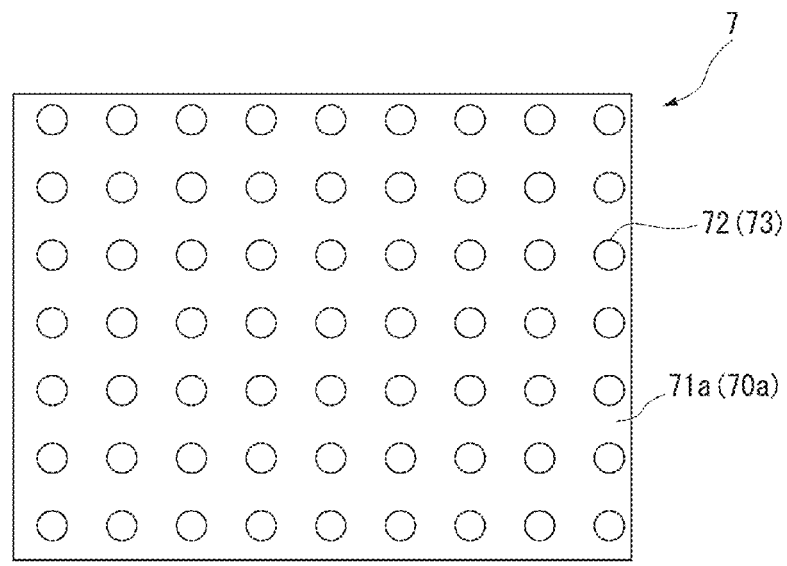
FIGS. 13A and 13B are schematic configuration diagrams showing modified examples of a sensor chip having the second protrusions.

As shown in FIG. 13A, two or more of the second protrusions 72 are formed on the upper face 71a of each of a plurality of the first protrusions (not shown). Two or more of the third protrusions 73 are formed on each of the plurality of the base portions 70a. In addition, the second protrusions 72 and the third protrusions 73 are arranged periodically in the fourth direction that intersects with the third direction and is parallel to the planar portion of the substrate. In this figure, as an example, a structure in which the second protrusion 72 and the third protrusion 73 have a circle shape in the plan view is represented. Alternatively, the second protrusions 72 and the third protrusions 73 may be randomly disposed without having any periodicity. It is preferable that the interval of the second protrusions 72 and the interval of the third protrusions 73 are set in the range of zero to several tens nm.

Figure 13B:
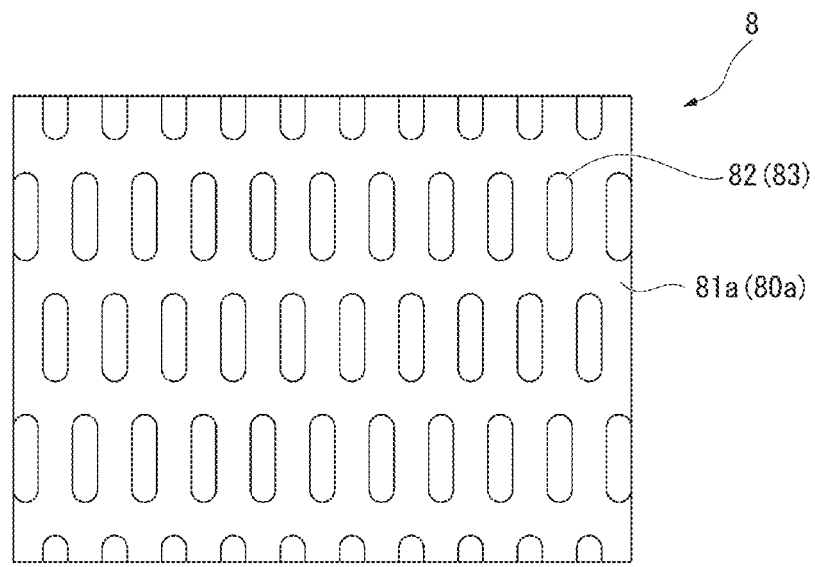

As shown in FIG. 13B, two or more of the second protrusions 82 are formed on the upper face 81a of each of a plurality of the first protrusions (not shown). Two or more of the third protrusions 83 are formed on each of the plurality of the base portions 80a. In addition, the second protrusions 82 and the third protrusions 83 are arranged periodically in the fourth direction that intersects with the third direction and is parallel to the planar portion of the substrate. In this figure, as an example, a structure in which the second protrusion 82 and the third protrusion 83 have an oval shape in the plan view is represented. Alternatively, the second protrusions 82 and the third protrusions 83 may be randomly disposed without having any periodicity. It is preferable that the interval of the second protrusions 82 and the interval of the third protrusions 83 are set in the range of zero to several tens of nm.

According to this configuration, the density in the space in which the enhanced electric filed is generated can be increased, compared to a case where the second protrusions and the third protrusions are formed only in the direction (the third direction) parallel to the planar portion of the substrate. Accordingly, a sensor chip capable of specifying a target substance from the SERS spectrum by improving the sensitivity of the sensor can be provided. Furthermore, in addition to the period of the second protrusions and the third protrusions in the third direction, the period in the fourth direction can be appropriately changed. Accordingly, the wavelength of the light emitted when specifying a target substance can be appropriately selected, whereby the width of the measurement range increases.

In addition, in this embodiment, the second protrusions and the third protrusions are formed by patterning the Au film formed on the upper face of the glass substrate. However, the invention is not limited thereto. For example, the second protrusions and the third protrusions may be fine particles. According to such a configuration, a sensor chip capable of specifying a target substance from the SERS spectrum by improving the sensitivity of the sensor can be provided.

In addition, in this embodiment, as the metal contained in the substrate, the metal contained in the first protrusion, the metal contained in the second protrusion, and the metal contained in the third protrusion, the same metal (gold or silver) is employed. However, the invention is not limited thereto. For example, different metals (gold, silver, copper, aluminum, or an alloy thereof) may be combined so as to be used, as in a case where the metal contained in the substrate is gold, the metal contained in the first protrusion is silver, and the metal contained in the second protrusion (the third protrusion) is an alloy of gold and silver or the like.

Analysis Apparatus

Figure 14:
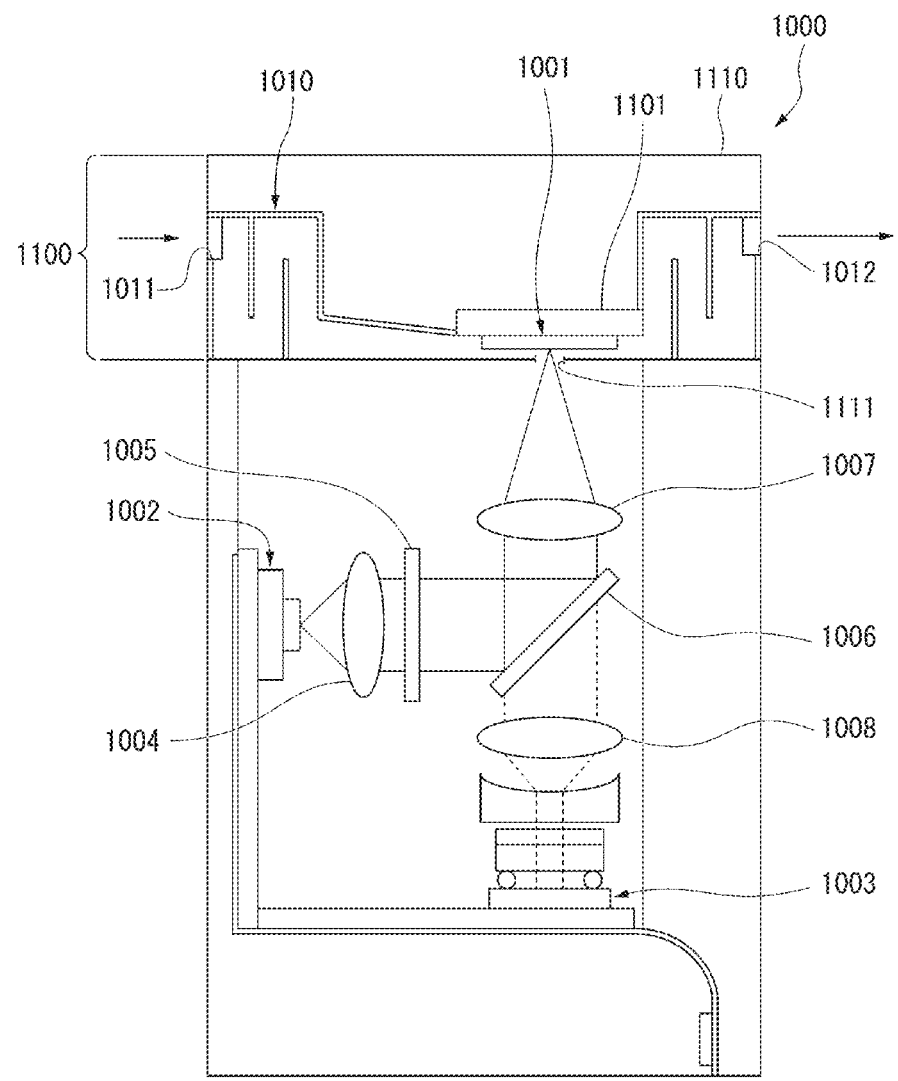
FIG. 14 is a schematic diagram representing an example of an analysis apparatus.

FIG. 14 is a schematic diagram representing an example of an analysis apparatus that includes a sensor chip according to an embodiment of the invention. In addition, arrows shown in FIG. 14 represent the transport direction of a target substance (not shown).

As shown in FIG. 14, the analysis apparatus 1000 includes a sensor chip 1001, a light source 1002, a photo detector 1003, a collimator lens 1004, a polarization control device 1005, a dichroic mirror 1006, an objective lens 1007, an objective lens 1008, and a transport unit 1010. The light source 1002 and the photo detector 1003 are electrically connected to a control device (not shown) through respective wirings.

The light source 1002 generates a laser beam that excites the SPP, the LSPR, and the SERS. The laser beam emitted from the light source 1002 becomes a parallel beam through the collimator lens 1004, passes through the polarization control device 1005, is guided in the direction of the sensor chip 1001 by the dichroic mirror 1006 so as to be collected to the objective lens 1007, and is incident to the sensor chip 1001. At this time, on the surface (for example, a face on which a metal nanostructure or a detection substance selecting mechanism is formed) of the sensor chip 1001, a target substance (not shown) is placed. In addition, by controlling the driving of a fan (not shown), the target substance is introduced into the inside of the transport unit 1010 from a loading entrance 1011 and is discharged from a discharge opening 1012 to the outside of the transport unit 1010. The size of the metal nanostructure is smaller than the wavelength of the laser beam.

When the laser beam is incident to the metal nanostructure, free electrons are in a state of resonant oscillation accompanying the oscillation of the laser beam, and a strong surface localized electric field is excited near the metal nanostructure, whereby the LSPR is excited. Then, when the distance between the metal nanostructures adjacent to each other is shortened, an extremely strong enhanced electric field is generated near the contact point. When one to several target substances are adsorbed on the contact point, the SERS occurs from the contact point.

The light (Raman scattering light or Rayleigh scattering light) scattered by the sensor chip 1001 passes through the objective lens 1007, is guided in the direction of the photo detector 1003 by the dichroic mirror 1006 so as to be collected to the objective lens 1007, and is incident to the photo detector 1003. Then, the light is resolved in a spectrum by the photo detector 1003, whereby spectrum information can be acquired.

According to this configuration, since a sensor chip according to an embodiment of the invention is included, the target molecule can be detected by performing selective spectroscopy for the Raman scattering light. Therefore, an analysis apparatus 1000 capable of specifying a target substance from the SERS spectrum by improving the sensitivity of the sensor can be provided.

The analysis apparatus 1000 includes a sensor cartridge 1100. The sensor cartridge 1100 includes the sensor chip 1001, the transport unit 1010 that transports a target substance to the surface of the sensor chip 1001, a placement unit 1101 in which the sensor chip 1001 is placed, and a casing 1110 that houses the above-described units. In a position of the casing 1110 that faces the sensor chip 1001, an irradiation window 1111 is disposed. The laser beam emitted from the light source 1002 passes through the irradiation window 1111 and is emitted to the surface of the sensor chip 1001. The sensor cartridge 1100 is located in the upper portion of the analysis apparatus 1000 and is detachably attached to the main unit of the analysis apparatus 1000.

According to this configuration, since the above-described sensor chip according to an embodiment of the invention is included, the target molecule can be detected by performing selective spectroscopy for the Raman scattering light. Therefore, a sensor cartridge 1100 capable of specifying a target substance from the SERS spectrum by improving the sensitivity of the sensor can be provided.

The analysis apparatus according to an embodiment of the invention can be broadly applied to detection of drugs or an explosive substances, medical treatments or physical examinations, and as a sensing apparatus used for inspection of foodstuffs. In addition, the analysis apparatus can be used as an affinity sensor or the like that detects whether or not a substance is adsorbed, including whether or not an antigen is adsorbed in an antigen-antibody reaction.

What is claimed is:

1. An analysis apparatus comprising:
a sensor chip wherein a substrate that has a planar portion, and a diffraction grating that includes a plurality of first protrusions periodically arranged in a period equal to or greater than 100 nm and equal to or less than 1000 nm in a first direction that is parallel to the planar portion, a plurality of base portions that is located between two of the first protrusions adjacent to each other and configures a base of the substrate, a plurality of second protrusions that is formed on upper faces of the plurality of the first protrusions, and a plurality of third protrusions that is formed on the plurality of base portions, has a surface formed from a metal, and is formed on the planar portion; and
a light source that emits light to the sensor chip wherein a wavelength of the light is longer than the period of the second protrusions and the third protrusions; and a photo detector that detects light acquired by the sensor chip.

2. The analysis apparatus sensor chip according to claim 1, wherein the plurality of the first protrusions is periodically arranged in a second direction that intersects with the first direction and is parallel to the planar portion.

3. The analysis apparatus according to claim 1, wherein the plurality of second protrusions and the plurality of third protrusions are periodically arranged in a third direction that is parallel to the planar portion.

4. The analysis apparatus to claim 3, wherein the plurality of second protrusions and the plurality of third protrusions are periodically arranged in a fourth direction that intersects with the third direction and is parallel to the planar portion.

5. The analysis apparatus to claim 1, wherein the plurality of second protrusions and the plurality of third protrusions are formed from micro-particles.

6. The analysis apparatus according to claim 1, wherein the metal that composes the surface of the diffraction grating is gold or silver.

7. The analysis apparatus according to claim 1, wherein a transport unit include a fan between entrance and a discharge opening, and a placement unit in which the sensor chip is placed, and a casing that houses the sensor chip, the transport unit, and the placement unit, and an irradiation window that is disposed at a position facing the surface of the sensor chip on the casing.

8. The analysis apparatus according to claim 1, wherein the light source generates a laser beam that excites Surface Plasmon Polariton, Localized Surface Plasmon Resonance, and a Surface Enhanced Raman Scattering.

9. The analysis apparatus comprising:
a sensor chip wherein a substrate that has a planar portion, and a diffraction grating, in which a target substance is placed, that has a composite pattern that is formed in the planar portion by superimposing a first concave-convex shape in which a plurality of first convex shapes is periodically arranged in a period equal to or greater than 100 nm and equal to or less than 1000 nm, a second concave-convex shape in which a plurality of second convex shapes is periodically arranged in the plurality of first convex shapes in a period shorter than that of the first concave-convex shape, and a third concave-convex shapes in which a plurality of third convex shapes is arranged periodically in a period shorter than that of the first concave-convex shape in a base portion located between two of the first convex shapes adjacent to each other, and has a surface formed from a metal; and a light source that emits light to the sensor chip wherein a wavelength of the light is longer than the period of the second convex shapes and the third convex shapes;

and a photo detector that detects light acquired by the sensor chip.

10. The analysis apparatus according to claim 9, wherein the plurality of first convex shapes is periodically arranged in a first direction that is parallel to the planar portion and is periodically arranged in a second direction that intersects with the first direction and is parallel to the planar portion.

11. The analysis apparatus according to claim 9, wherein the plurality of second convex shapes and the plurality of third convex shapes are periodically arranged in a third direction that is parallel to the planar portion.

12. The analysis apparatus according to claim 11, wherein the plurality of second convex shapes and the plurality of third convex shapes are periodically arranged in a fourth direction that intersects with the third direction and is parallel to the planar portion.

13. The analysis apparatus according to claim 9, wherein the plurality of second convex shapes and the plurality of third convex shapes are formed from micro-particles.

14. The analysis apparatus according to claim 9, wherein the metal that composes the surface of the diffraction grating is gold or silver.

15. The analysis apparatus according to claim 9, wherein a transport unit include a fan between entrance and a discharge opening, and a placement unit in which the sensor chip is placed, and a casing that houses the sensor chip, the transport unit, and the placement unit, and an irradiation window that is disposed at a position facing the surface of the sensor chip on the casing.

16. The analysis apparatus according to claim 1, wherein the light source generates a laser beam that excites Surface Plasmon Polariton, Localized Surface Plasmon Resonance, and a Surface Enhanced Raman Scattering.

* * * * *